United States Patent [19]
Amedio et al.

[11] Patent Number: 5,919,967
[45] Date of Patent: *Jul. 6, 1999

[54] PROCESS FOR SYNTHESIZING PHOSPHODIESTERS

[75] Inventors: John C. Amedio, Franklin, Mass.; Paul J. Bernard, East Setaukset, N.Y.; Mark Fountain, Mantua, N.J.

[73] Assignee: EPIX Medical, Inc., Cambridge, Mass.

[ * ] Notice: This patent issued on a continued prosecution application filed under 37 CFR 1.53(d), and is subject to the twenty year patent term provisions of 35 U.S.C. 154(a)(2).

[21] Appl. No.: 08/833,745

[22] Filed: Apr. 11, 1997

[51] Int. Cl.$^6$ ............................... C07F 9/117; C07F 9/09
[52] U.S. Cl. .................. 558/122; 536/25.34; 556/26; 558/169
[58] Field of Search ................... 558/122, 169; 556/26

[56] References Cited

U.S. PATENT DOCUMENTS

| | | |
|---|---|---|
| 4,647,447 | 3/1987 | Gries et al. . |
| 4,880,008 | 11/1989 | Lauffer . |

FOREIGN PATENT DOCUMENTS

| | | |
|---|---|---|
| WO-96/23526 | 8/1996 | WIPO . |
| WO-96/27379 | 9/1996 | WIPO . |

OTHER PUBLICATIONS

Hengge et al., "Studies of Transition–State Structures in Phosphoryl Transfer Reactions of Phosphodiesters of p–Nitrophenol," *J. Am. Chem. Soc.*, vol. 117 (22), pp. 5919–5926 (1995).

Lu et al., "A New, Convenient and Efficient Procedure For The Synthesis Of Phosphodiesters Using Chloro–N,N–diisopropylaminoalkyloxyphospines, " *Synth. Commun.*, vol. 23 (14), pp. 1943–1946 (1993).

Martin et al., "Fluorination of Methoxydichlorophosphines," *J. Am. Soc. Chem.*, vol. 72, pp. 4584–4586 (1950).

Bannwarth et al., "A Simple and Effective Chemical Phosphorylation Procedure for Biomolecules," *Helv. Chimica Acta*, vol. 70, pp. 175–186 (1987).

Bannwarth et al., "Bis(allyloxy)(diisopropylamino)phosphine as a new Phosphinylation Reagent for the Phosphorylation of Hydroxy Functions," *Tet. Letters*, vol. 30, No. 32, pp. 4219–4222 (1989).

Beaucage et al., "Advances in the Synthesis of Oligonucleotides by the Phosphoramidite Approach," *Tetrahedron*, vol. 48, No. 12, pp. 2223–2311 (1992).

Beaucage et al., "The Synthesis of Specific Ribonucleotides and Unrelated Phosophorylated Biomolecules by the Phosphoramidite Approach," *Tetrahedron*, vol. 49, No.46, pp. 10441–10488 (1993).

Desseaux et al., "Synthesis of Phosphodiester and Triester Derivatives of AZT with Tethered N–Methyl Piperazine and N,N,N' Trimethylethylenediamine," *Bioorg.&Med. Chem. Letters*, vol. 3, No. 8, pp. 1547–1550 (1993).

Garcia et al., "Synthesis of New Ether Glycerophosopholipids Structurally Related to Modulator," *Tetrahedron*, vol. 47, No. 48, pp. 10023–10034 (1991).

Garigapati et al., "Synthesis of Short Chain Phosphatidylinositols," *Tet. Letters*, vol. 34, No. 5, pp. 769–772 (1993).

Grote et al., "Stereocontrolled Synthesis of DTPA Analogues Branched in the Ethylene Unit," *J. Org. Chem.*, 60:6987–97 (1995).

Hebert et al., "A New Reagant for the Removal of the 4–Methoxybenzyl Ether: Application of the Synthesis of Unusual Macrocyclic and Bolaform Phosphatidylcholines," *J. Org. Chem.*, 57:1777–83 (1992).

Kang et al., "Synthesis, Characterization, and Crystal Structure of the Gadolinium (III) Chelate of (1R,4R,7R)–α,α', α"–Trimethyl–1,4,7,10–tetraazacyclododecane–1,4,7–triacetic Acid (DO3MA)," *Inorg. Chem.*, 32:12–18 (1993).

Kazi et al., "Synthesis of Phosphoserine and Phosphothreonine Ether–Glycerolipids via 2,2,2–Trichloro–t–Butyl Phosphodicloridite Coupling," *Tet. Letters*, vol. 33, No. 17, pp. 2291–2294 (1992).

Lammers et al., "Synthesis of Phospholipids via Phosphotriester Intermediates," *J. Royal Netherlands Chem. Soc.*, 98/4 (1979).

Lindh et al., "A General Method for the Synthesis of Glycerophospholipids and their Analogues via H–Phosphonate Intermediates," *J. Org. Chem.*, 54:1338–42 (1989).

Maritn et al. "A General Protocol for the Preparation of Phospholipids via Phosphite Coupling," *Tet. Letters*, vol. 29, No. 30, pp. 3631–3634 (1988).

Martin et al., "General Method for the Synthesis of Phospholipid Derivatives of 1,2–O–Diacyl–sn–glycerols," *J. Org. Chem.*, 59:4805–20 (1994).

(List continued on next page.)

*Primary Examiner*—Michael G. Ambrose
*Attorney, Agent, or Firm*—Fish & Neave

[57] ABSTRACT

A process for preparing a phosphodiester of the formula:

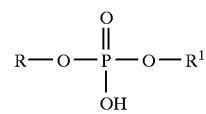

is described that involves (1) reaction of a first alcohol with phosphorous trichloride to form a phosphorodichlorodite, (2) reaction of the phosphorodichlorodite with an amine to form a phosphorodiamidite, (3) reaction with a second alcohol (which may be the same as the first alcohol) to form a phosphoramidite diester, and finally, (4) hydrolysis and oxidation of the phosphoramidite to form the phosphodiester. R and R1 may represent aliphatic, aromatic, heterocyclic, peptidic, peptoid, deoxyribo- or ribonucleotidic or nucleosidic, or organic chelating moieties.

17 Claims, No Drawings

OTHER PUBLICATIONS

Martin et al., "Synthesis and Kinetic Evaluation of Inhibitors of the Phosphatidylinositol–Specific Phospholipase C from *Bacillus cereus*," *J. Org. Chem.*, 61:8016–23 (1996).

Moore et al., "Conceptual Basis of the Selective Activation of Bis(dialkylamino)methoxyphosphines by Weak Acids and Its Application toward the Preparation of Deoxy-nucleoside Phosphoramidites in Situ," *J. Org. Chem.*, 50:2019–25 (1985).

Pirrung et al., "Inverse Phosphotriester DNA Synthesis Using Photochemically–Removable Dimethoxybenzoin Phosphate Protecting Groups," *J. Org. Chem.*, 61:2129–36 (1996).

Ramirez et al., "Synthesis of Phosphodiesters: The Cyclic Enediol Phosphoryl (CEP) Method," *Synthesis*, pp. 449–488 (1985).

PROCESS FOR SYNTHESIZING PHOSPHODIESTERS

FIELD OF THE INVENTION

The present invention relates to an improved process for the production of phosphodiester compounds. In particular, the invention relates to an improved process for preparing phosphodiester compounds which are useful as contrast agents for diagnostic imaging, and more particularly, for preparing diethylenetriamine-pentaacetic acid ("DTPA") compounds comprising phosphodiesters.

BACKGROUND OF THE INVENTION

Many important biological substances, including phospholipids, oligonucleotides, deoxynucleosides, nucleotides and nucleosides, exist as symmetrical and unsymmetrical phosphodiesters. The usefulness of such phosphodiester compounds in medical applications is well known. See, e.g., Desseaux et al., "Synthesis of Phosphodiester and Triester Derivatives of AZT with Tethered N-Methyl Piperazine and N,N,N'trimethylethylenediamine," *Bioorg. & Med. Chem. Letters,* vol. 3, no. 8, pp. 1547–50 (1993); PCT publication no. WO 96/27379. Recently, PCT publication no. WO 96/23526, incorporated herein by reference, describes phosphodiester compounds which are useful as contrast agents for diagnostic imaging.

A number of methods of making phosphodiester compounds, based on P(III) chemistry, are known. In general, phosphorylation plays an important role in the synthesis of phosphodiester compounds. But the known phosphodiester synthetic methods all suffer from a number of problems including how phosphorylation is accomplished.

One method for making phosphodiesters involves the use of phosphoramidite chemistry. See, e.g., Bannwarth et al., "A Simple and Effective Chemical Phosphorylation Procedure for Biomolecules," *Helvetica Chimica Acta,* vol. 70, pp. 175–186 (1987); Bannwarth et al., "Bis(allyloxy) (diisopropylamino) phosphine as a New Phosphinylation Reagant of the Phosphorylation of Hydroxy Functions," *Tetrahedron Letters,* vol. 30, no. 32, pp. 4219–22 (1989); Moore et al., "Conceptual Basis of the Selective Activation of Bis(dialkylamino) methoxyphosphines by Weak Acids and Its Application toward the Preparation of Deoxynucleoside Phosphoramidites in Situ," *J.Org.Chem.,* vol. 50, pp. 2019–2025 (1985); Hebert et al., "A New Reagant for the Removal of the 4-Methoxybenzyl Ether: Application to the Synthesis of Unusual Macrocyclic and Bolaform Phosphatidycholines," *J.Org.Chem.,* vol. 57, pp. 1777–83 (1992); Desseaux et al., "Synthesis of Phosphodiester and Triester Derivatives of AZT with Tethered N-Methyl Piperazine and N,N,N'trimethylethylenediamine," *Bioorg. & Med. Chem. Letters,* vol. 3, no. 8, pp. 1547–50 (1993); Pirrung et al., "Inverse Phosphotriester DNA Synthesis Using Photochemically-Removable Dimethoxybenzoin Phosphate Protecting Groups," *J.Org.Chem.,* vol. 61, pp. 2129–36 (1996).

Such phosphoramidite methods, however, suffer from the fact that the phosphoramidites are typically unstable compounds (both chemically and kinetically) and upon purification by distillation may ignite or cause an explosion. Further, phosphoramidite methods are generally not suitable for manufacturing phosphodiester compounds on a commercial basis. This is so because the phosphoramidite starting materials are very expensive and are not readily available, and because methods using phosphoramidites tend to involve additional process steps (e.g., additional step of cleaving protecting groups after phosphorylation) as well as multiple isolation and/or purification steps of the intermediates.

Methods involving the use of phosphodichloridates as the phosphorylating agent suffer from similar problems. See, e.g., Martin et al., "General Method for the Synthesis of Phospholipid Derivatives of 1,2-O-Diacyl-sn-glycerols," *J.Org.Chem.,* vol. 59, pp. 4805–20 (1994); Martin et al., "A General Protocol for the Preparation of Phospholipids via Phosphate Coupling," *Tetrahedron Letters,* vol. 29, no. 30, pp. 3631–34 (1988); Lammers et al., "Synthesis of Phospholipids via Phosphotriester Intermediates," *J.Roya Netherlands Chem. Soc'y,* 98/4, pp. 243–250 (April 1979); Martin et al., "Synthesis and Kinetic Evaluation of Inhibitors of the Phosphatidylinositol-Specific Phospholipase C from *Bacillus cereus,*" *J.Org.Chem.,* vol. 61, pp. 8016–23 (1996).

Another method used for making phosphodiester compounds involves the use of $PCl_3$ to generate hydrogenphosphonate intermediates. See, e.g., Lindh et al., "A General Method for the Synthesis of Glycerophospholipids and Their Analogues via H-Phosphonate Intermediates," *J.Org.Chem.,* vol. 54, pp. 1338–42 (1989); Garcia et al., "Synthesis of New Ether Glycerophospholipids Structurally Related to Modulator," *Tetrahedron,* vol. 47, no. 48, pp. 10023–34 (1991); Garigapati et al., "Synthesis of Short Chain Phosphatidylinositols," *Tetrahedron Letters,* vol. 34, no. 5, pp. 769–72 (1993). This method, however, requires the use of a coupling reagent which can either be purchased or independently synthesized, and thus renders such methods expensive or more complex. In addition, multiple isolation and purification steps of the intermediates are required, often with laborious drying conditions for the H-phosphonate intermediate.

Consequently, there remains a need for a safe, efficient and inexpensive process for the production, in high yields, of phosphodiester compounds with the potential of having a wide variety of substituents which does not require either the use of a protecting group or a coupling agent. In particular, there remains a need for a process which could be performed in one reaction vessel and does not require multiple isolation and purification steps because of the formation of multiple intermediates.

SUMMARY OF THE INVENTION

The present invention relates to a safer, more efficient and less expensive process for preparing phosphodiester compounds, and more particularly, phosphodiesters having the formula:

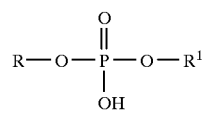

In accordance with the present invention, the process comprises the steps of:

(a) coupling $PCl_3$ with an alcohol to obtain a substituted dichlorophosphine;

(b) coupling of said dichlorophosphine with an amine base to obtain a bis(amino)phosphino;

(c) coupling of said bis(amino)phosphino with a second alcohol, which can be the same or different from that alcohol used in step (a), to obtain a disubstituted (amino)phosphino;

(d) and reacting said (amino)phosphino with water and an oxidant to obtain the desired phosphodiester compound.

The process according to this invention avoids the use of unstable phosphorylating agents as well as the need for using a protecting group or a coupling agent. Thus, the present method avoids unnecessary process steps such as deprotection and coupling reagent syntheses. In a preferred embodiment of this invention, the phosphodiester synthetic process takes place in one reaction vessel, avoiding the need for multiple isolation and/or purification steps.

DETAILED DESCRIPTION OF THE INVENTION

In order that the invention herein described may be more fully understood, the following detailed description is set forth.

The present invention provides an improved process for preparing phosphodiester compounds of general formula:

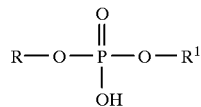

where R and $R^1$ can be the same or different and are selected from the group consisting of linear, branched, or cyclic aliphatic, aryl, heterocyclic, peptidic, peptoid, deoxyribo- or ribo-nucleotidic or nucleosidic, or cyclic or acyclic organic chelating agent groups, all of which may optionally be substituted with one or more nitrogen, oxygen, sulfur, halogen, aliphatic, amide, ester, sulfonamide, aryl, acyl, sulfonate, phosphate, hydroxyl, or organometallic substituents.

In a preferred aspect of the invention, all synthetic steps are performed in one reaction vessel, precluding the need for multiple isolation and/or purification steps. The present invention demonstrates an efficient and high-yielding process for producing phosphodiester compounds which does not rely on expensive or unstable starting materials and does not require the use of either protecting groups or coupling agents. Moreover, said process is efficient for the generation of phosphodiester linkages between a wide variety of substituents.

Process Scheme

In accordance with this invention, an alcohol ROH, where R has the same meaning as stated above, is reacted with $PCl_3$, preferably at a molar ratio of 1:1, to form a dichlorophosphine reaction product (I):

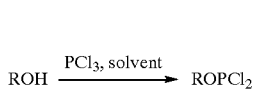

(I)

This reaction takes place in the presence of an ethereal or hydrocarbon solvent and is carried out at a temperature of from about −50° C. to about 15° C., preferably from about −10° C. to about −5° C., for a period of from about 30 minutes to about 3 hours, preferably from about 1 to about 1.5 hours. The solvent may be any ethereal or hydrocarbon solvent and preferably, may be selected from the group consisting of heptanes, methyl-t-butyl ethers, dioxanes, tetrahydrofurans, diethyl ethers, and ethylene glycol dialkyl ethers. More preferably, the solvent is tetrahydrofuran.

The dichlorophosphine (I) is then reacted with from about 5 to about 6 equivalents of an amine base to form a bis(amino)phosphino reaction product (II):

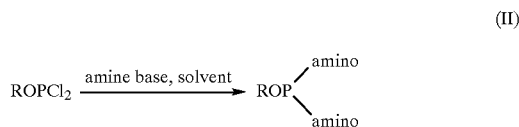

(II)

This reaction also takes place in the presence of an ethereal or hydrocarbon solvent, as described above, and is carried out at a temperature of from about −50° C. to about 15° C., preferably from about −10° C. to about −5° C., for a period of from about 30 minutes to about 3 hours, preferably from about 15 to about 30 minutes. The base used to form reaction product (II) may be any amine base, preferably a base having a pKa value of from about 5 to about 11, and more preferably selected from the group consisting of imidazole, 2,4-dimethylimidazole, 1H-tetrazole, dialkylamines (methyl, ethyl, butyl), pyridine, piperazine, piperidine, pyrrole, 1H-1,2,3-triazole, and 1,2,4-triazole. In a more preferred embodiment, the base is imidazole.

The bis(amino)phosphino compound (II) is then reacted with from about 0.75 to about 1.0 equivalents of a second alcohol $R^1OH$, where $R^1$ has the same meaning as stated above, to form an (amino)phosphino reaction product (III):

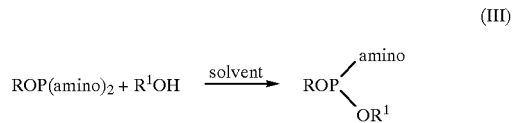

(III)

This reaction takes place in the presence of an ethereal or hydrocarbon solvent and carried out at a temperature of from about −50° C. to about 15° C., preferably from about −10° C. to about −5° C., for a period of from about 30 minutes to about 3 hours, preferably from about 1.0 to about 1.5 hours. The solvent may be any ethereal or hydrocarbon solvent and preferably may be selected from the group consisting of heptanes, methyl-t-butyl ethers, dioxanes, tetrahydrofurans, 1,3-dioxolanes, diglymes, diethyl ethers, dialkyl ethers, and ethylene glycol dialkyl ethers. More preferably, the solvent is tetrahydrofuran.

Finally, the (amino)phosphino compound (III) is reacted with about one equivalent of acidic water, preferably having a pH of about 2.5 to about 5, and about 1 or more equivalents of an oxidant to form the desired phosphodiester compound (IV):

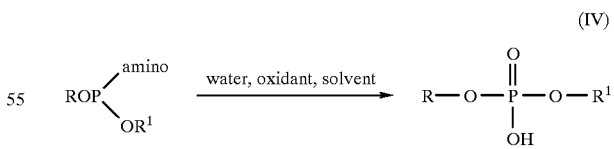

(IV)

The oxidant may be any peroxide type oxidant and preferably selected from the group consisting of periodates. More preferably, the oxidant is sodium periodate.

The above hydrolysis and oxidation is carried out in a solvent mixture at a temperature of from about −15° C. to about 25° C., preferably from about 0° C. to about 2° C., for a period of from about 10 to about 24 hours, preferably from about 10 to about 15 hours. The solvent mixture comprises any combination of solvents selected from the group consisting of ethereal or hydrocarbon solvents. Preferably, the solvent mixture comprises tetrahydrofuran, heptane and toluene in the volume ratio of 10:10:1.

Use of the Process Products

It has been found that the above process is particularly useful in the preparation of contrast agents for diagnostic imaging. Examples of phosphodiester contrast agents that may be prepared by this improved process include the compounds shown below, as well as others described in PCT publication no. WO 96/23 526.

MS-315
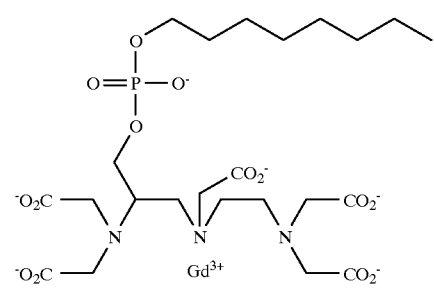

MS-317
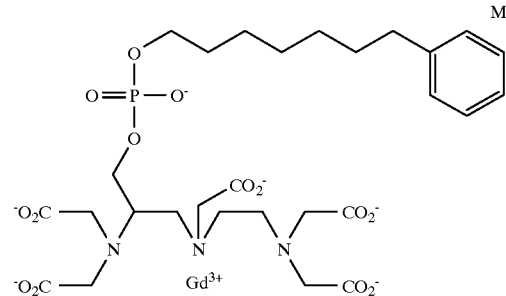

MS-322
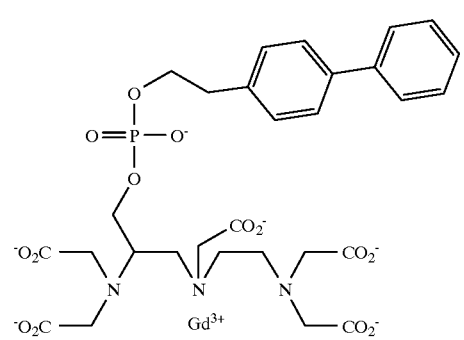

MS-323
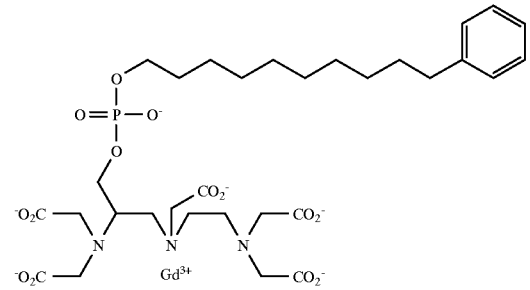

MS-325
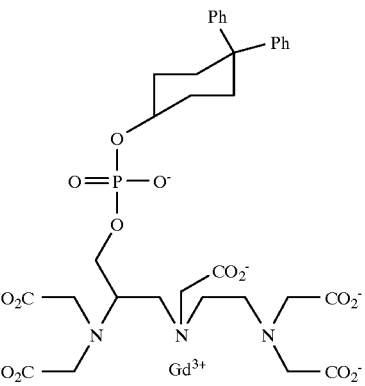

MS-326
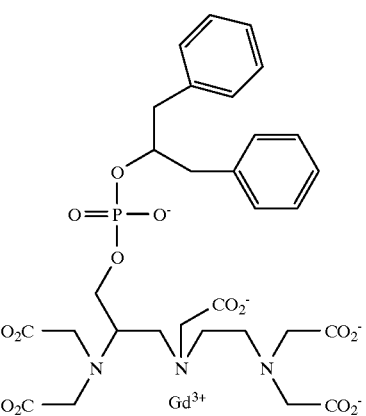

MS-327
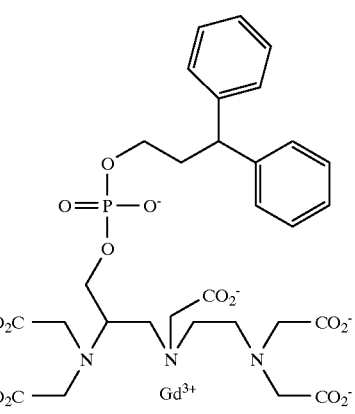

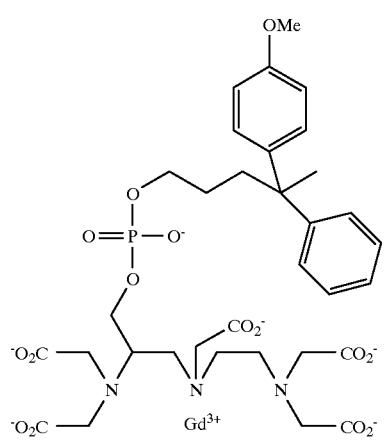

MS-328

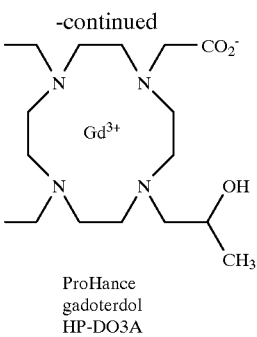

ProHance
gadoterdol
HP-DO3A

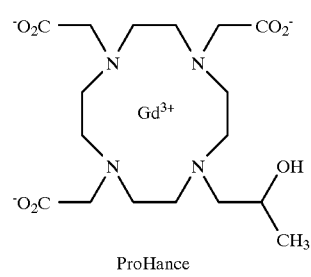

ProHance
gadoterdol
HP-DO3A

In such cases, it is contemplated that at least one of the two alcohols (ROH, R$^1$OH) as defined herein further comprise a cyclic or acyclic organic chelating ligand, with any sensitive functional groups (e.g., carboxylates) on such a chelate protected with appropriate groups (e.g., t-butyl groups). Suitable chelating ligands are well known in the art. For example, where the phosphodiester compound is to be used as a contrast agent for magnetic resonance imaging, preferred chelating ligands include:

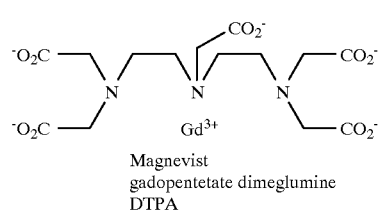

Magnevist
gadopentetate dimeglumine
DTPA

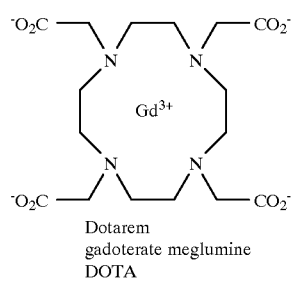

Dotarem
gadoterate meglumine
DOTA

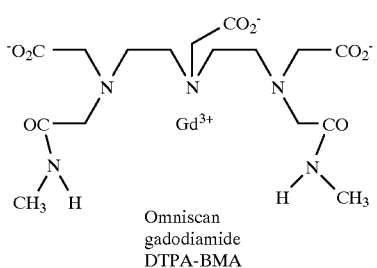

Omniscan
gadodiamide
DTPA-BMA

The removal of any protecting groups on the chelate as well as the complexation of the chelate with the desired metal can be performed after carrying out the phosphodiester synthetic process of this invention by methods well known in the art. See, e.g., Grote et al., "Stereocontrolled Synthesis of DTPA Analogues Branged in the Ethylene Unit," *J. Org. Chem.*, 60:6987–97 (1995); Kang et al., "Synthesis, Characterization, and Crystal Structure of the Gadolinium (III) Chelate of(1R,4R,7R)-α,α',α''-Trimethyl-1,4,7,10-tetraazacyclododecane- 1,4,7-triacetic Acid (DO3MA)," *Inorg. Chem.*, 32:2912–18 (1993) and references cited therein.

It is also contemplated that for such phosphodiester contrast agents, the alcohol (ROH or R$^1$OH) may comprise a moiety designed to facilitate localization of the resultant agent to the tissue, cell, protein, receptor or area desired to be imaged. Examples of such moieties include lipophilic or amphiphilic substances, receptor ligands, antibodies, or antibody fragments, peptides, or other biomolecules that are known to concentrate in the specific biological component desired to be imaged.

In order that this invention may be better understood, the following example is set forth. This example is for purposes of illustration only and is not intended to limit the scope of this invention in any way.

EXAMPLE

The preparation of [(4,4-diphenylcyclohexyl) phosphooxymethyl] diethylene triaminepenta-acetic acid is shown below in Scheme I:

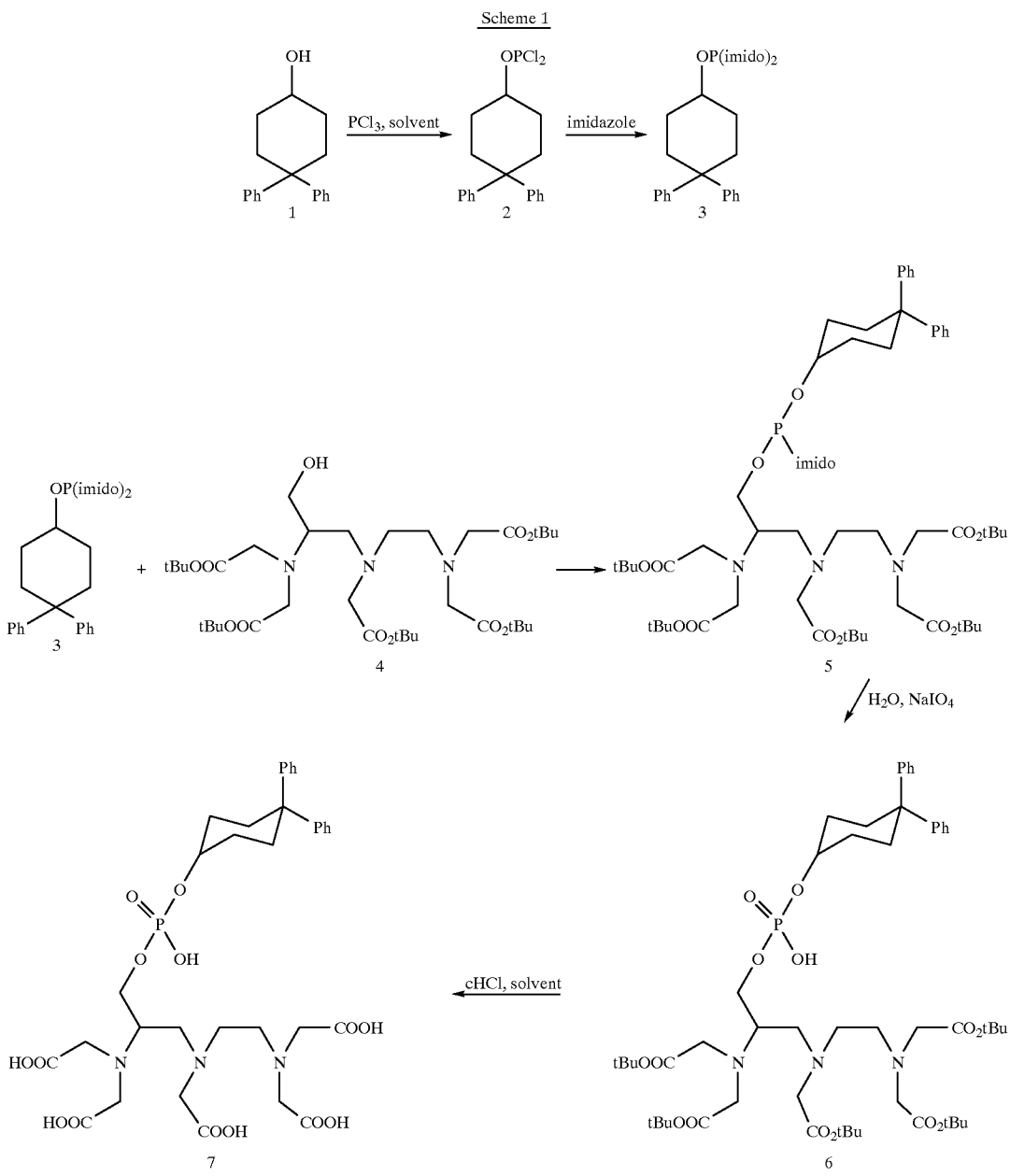

Scheme 1

In a single reaction vessel that contained a solution of phosphorous trichloride (13.2 mL, 0.151 mol) in tetrahydrofuran (202 ml) was added a solution of 4,4-diphenylcyclohexanol (1) (38.34 g, 0.152 mol) in tetrahydrofuran (243 ml) while stirring and maintaining an internal temperature of −6.2° C. to −5.3° C. for 1.5 hours. The mixture was then stirred for an additional 34 minutes yielding a dichlorophosphine reaction product (2), having a $^{31}$P NMR chemical shift of 174.28 ppm.

To this solution, imidazole (51.34 g, 0.753 mol) in tetrahydrofuran (243 ml) was added while stirring and maintaining an internal temperature of −7.8° C. to −3.6° C. for 37 minutes. The resulting mixture was then stirred for an additional 20 minutes yielding a solution of a bis(amino) phosphino reaction product (3) having a $^{31}$P NMR chemical shift of 106.36 ppm.

To this mixture was added a solution consisting of 2-(R)-hydroxymethyldiethylenetriamine pentaacetic acid, penta-t-butyl ester (4) (160.0 g, 0.128 mol, purity: 56.32% by weight) in heptane (114 ml) while stirring and maintaining an internal temperature of −6.8° C. to −4.8° C. for 1 hour and 6 minutes. This mixture was then stirred for an additional 23 minutes yielding a solution (5) having a $^{31}$P NMR chemical shift of 123.8 ppm.

Finally, water (202 ml) was added over a period of about 1 minute while maintaining an internal temperature of −6.5° C. to 6.5° C. The mixture was stirred for 5 minutes followed by the addition of heptane (620 ml), toluene (70 ml) and 5N aqueous hydrochloric acid (202 ml) over 5 minutes while maintaining an internal temperature of 1.0° C to 12.1 ° C.

Sodium periodate (22.6 g, 0.106 mol) was then added over a period of 3 minutes while maintaining an internal temperature of 10.5° C. The reaction mixture was warmed to room temperature over 35 minutes and stirred an additional 2.5 hours yielding a solution (6) with a $^{31}$P NMR chemical shift of 4.27 ppm. The layers were separated and the organic layer was washed with 10% aqueous sodium thiosulfate (2×809 mL).

To the above organic layer was added tetraoctylammonium bromide (8.21 g, 0.015 mol). Concentrated hydrochloric acid (11.51 M, 405 mL) was then added over a period of 22 minutes while maintaining an internal temperature of 22.8° C. to 25.0° C. This mixture was stirred for 16.0 hours yielding a compound (7) with a $^{31}$P NMR chemical shift of 7.78 ppm. The layers were separated and the organic layer discarded.

To the above aqueous layer was added 8M aqueous sodium hydroxide (630 mL) until a pH of 6.56 was recorded. The solution was concentrated under reduced pressure (50° C. to 55° C., vacuum 85 mm Hg) until 400 mL of solvent was collected (approximately 1 hour). The solution was cooled to room temperature and amberlite XAD-4 resin (92.0 g) was added. The suspension was stirred for 50 minutes at room temperature and filtered to give a light yellow aqueous solution (1.1 L).

The above solution was loaded onto C-18 reversed phase silica gel (271 g, packed wet in methanol and then washed with 800 mL methanol, 800 mL methanol/water, 1:1 and 800 mL water) and eluted with water. The first 1.0 L of elutent collected was discarded and the next 1.3 L collected were retained. To the retained solution was added 6N aqueous hydrochloric acid (60 mL to a pH=2.15) and 3N aqueous hydrochloric acid (30 mL to a pH=1.63). The slurry was stirred for 1.25 hours and filtered. The solid was washed with pH 1.67 aqueous solution (500 mL) and dried (48–50° C., 4–6 mm Hg) to a constant weight (18.0 hours) to obtain an off-white solid, compound of formula:

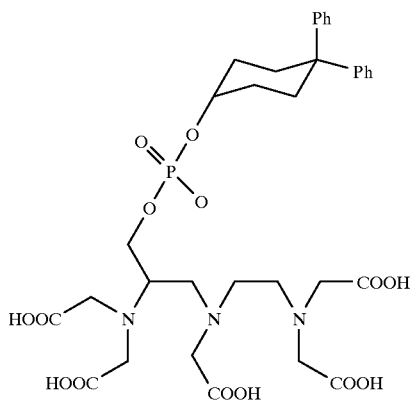

(65.5 g, Yield: 68.89% Purity: 99.45% by weight, 98.95% by area, 3.02% water and 97.81% chelatables).

We claim:

1. A process for preparing a phosphodiester compound having the formula:

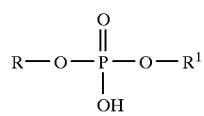

where R and R$^1$ may be the same or different and are chosen from the group consisting of linear, branched, or cyclic aliphatic; aryl; heterocyclic; peptidic; peptoid; deoxyribo- or ribo-nucleotidic or nucleosidic; and cyclic or acyclic organic chelating groups, all optionally substituted with one or more nitrogen, oxygen, sulfur, halogen, aliphatic, amide, ester, sulfonamide, aryl, acyl, sulfonate, phosphate, hydroxyl, or organometallic substituents, comprising the steps of:

(a) reacting an alcohol ROH with PCl$_3$ in the presence of a solvent to form a dichlorophosphine compound having the formula:

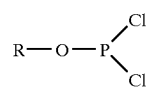

(b) coupling of the dichlorophosphine compound formed in step (a) with an amine base in the presence of a solvent to form a bis(amino)phosphino compound having the formula:

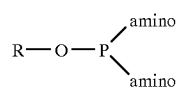

(c) coupling of the bis(amino)phosphino compound formed in step (b) with a second alcohol R$^1$OH, in the presence of a solvent, where the second alcohol can be the same or different from that of step (a), to form an (amino)phosphino compound having the following formula:

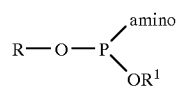

(d) and subjecting the (amino)phosphino compound formed in step (c) to hydrolysis and oxidation.

2. The process according to claim 1 wherein the phosphodiester compound is prepared in one reaction vessel.

3. The process according to either claim 1 or 2, in which, the alkoxydichlorophosphine compound formed in step (a) is reacted with from about 5 to about 6 equivalents of the amine base.

4. The process according to either claim 1 or 2, wherein the amine base has a pKa value of from about 5.0 to about 11.0.

5. The process according to claim 4, wherein the base is selected from the group consisting of imidazole, 2,4-dimethylimidazole, 1H-tetrazole, dialkylamines, pyridine, piperazine, piperidine, pyrrole, 1H-1,2,3-triazole, and 1,2,4-triazole.

6. The process according to claim 5, wherein the base is imidazole.

7. The process according to either claim 1 or 2, in which about one equivalent of ROH is reacted with about one equivalent of PCl$_3$.

8. The process according to either claim 1 or 2, wherein the solvent used in steps (a), (b) and (c) may be the same or different and is be selected from the group consisting of ethereal and hydrocarbon solvents.

9. The process according to claim 8, wherein the solvent is selected from the group consisting of heptanes, methyl-t-butyl ethers, dioxanes, tetrahydrofurans, 1,3-dioxolane, diglymes, diethyl ethers, dialkyl ethers, and ethylene glycol dialkyl ethers.

10. The process according to claim 9, wherein the solvent is tetrahydrofuran.

11. The process according to either claim 1 or 2, wherein the alkoxy(amino) phosphino compound formed in step (b) is coupled with about 1 equivalent of $R^1OH$.

12. The process according to either claim 1 or 2, wherein the hydrolysis and oxidation of the dialkoxy (amino) phosphino compound formed in step (c) is performed with water and an oxidant in a solvent at a temperature range of about $-15°$ C. to about $25°$ C. for a period of 10 to 24 hours.

13. The process according to claim 12, wherein the oxidant comprises sodium periodate.

14. The process according to claim 12, wherein the solvent comprises a mixture of tetrahydrofuran, heptane and toluene.

15. A process for preparing (4,4-diphenylcyclohexyl) phosphonooxymethyl diethylene triamine, penta t-butyl ester comprising the steps of:

(a) reacting 4,4-diphenylcyclohexanol with $PCl_3$ to obtain 4,4-diphenylcyclohexyloxy dichlorophosphine having the formula:

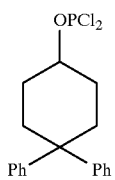

(b) coupling the 4,4-diphenylcyclohexyloxy-dichlorophosphine formed in step (a) with an amine base to obtain 4,4-diphenylcyclohexyloxydiaminophosphine having the formula:

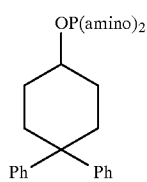

(c) coupling of the 4,4-diphenylcyclohexyloxy-diaminophosphine formed in step (b) with hydroxymethyl-DTPA penta tert-butyl ester to obtain 4,4-diphenylcyclohexyloxy (hydroxymethyl-DTPA-oxy, penta tert-butyl ester)amino-phosphine having the formula:

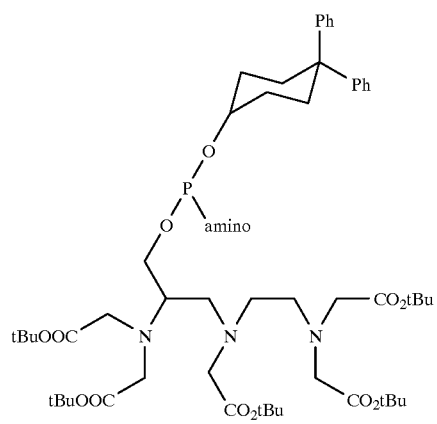

(d) hydrolysis and oxidation of the 4,4-diphenylcyclohexyloxy (hydroxymethyl-DTPA oxy, penta tert butyl ester) aminophosphine formed in step (c) with dilute HCl and an oxidant to form (4,4-diphenylcyclohexyl)phosphonooxymethyl diethylene triamine, penta t-butyl ester having the formula:

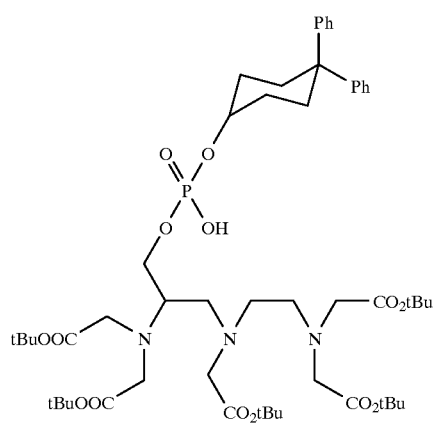

16. A process for preparing (4,4-diphenylcyclohexyl) phosphooxymethyl diethylene triaminepenta-acetic acid comprising the steps of:

(a) phosphorylating 1.0 equivalents of 4,4-diphenylcyclohexanol with about one equivalent of phosphorous trichloride to obtain 4,4-diphenylcyclohexyloxy dichlorophosphine having the formula:

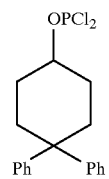

(b) coupling the 4,4-diphenylcyclohexyloxy-dichlorophosphine formed in step (a) with from about 5 to about 6 equivalents of imidazole to obtain 4,4-diphenycyclohexyloxy-diimidazolylphosphine having the formula:

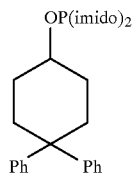

where imido refers to imidazolyl (c) coupling of the 4,4-diphenylcyclohexyloxy- diimidazolylphosphine formed in step (b) with from about 0.75 to about 1.0 equivalents of hydroxymethyl-DTPA penta tert-butyl ester to obtain 4,4-diphenylcyclohexyloxy (hydroxymethyl-DTPA -oxy, penta tert-butyl ester) imidazolyl-phosphine having the formula:

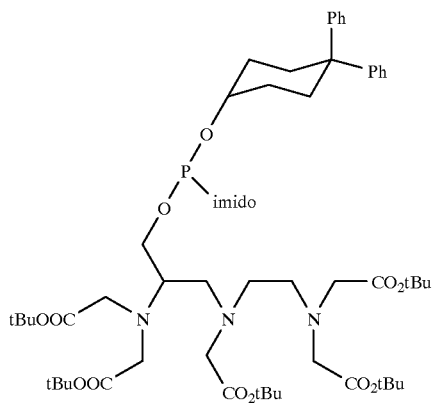

where imido refers to imidazolyl (d) hydrolysis and oxidation of the 4,4-diphenylcyclohexyloxy (hydroxymethyl-DTPA oxy, penta tert butyl ester) imidazolylphosphine formed in step (c) with dilute HCl and from about 0.5 to about 2.0 equivalents to sodium periodate to form (4,4-diphenylcyclohexyl)phosphonooxymethyl diethylene triamine, penta t-butyl ester having the formula:

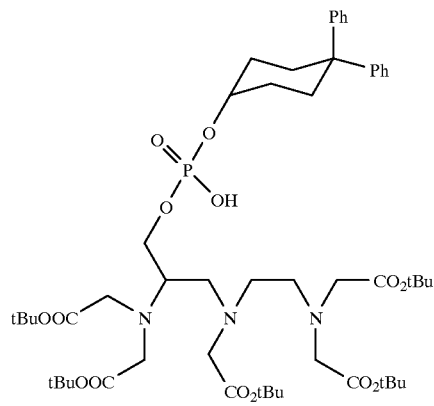

17. The process according to claim 16, further comprising the step of hydrolysis of the diethylenetriamine, penta t-butyl ester formed in step (d) in HCl to form diethylene triaminepentaacetic acid having the formula:

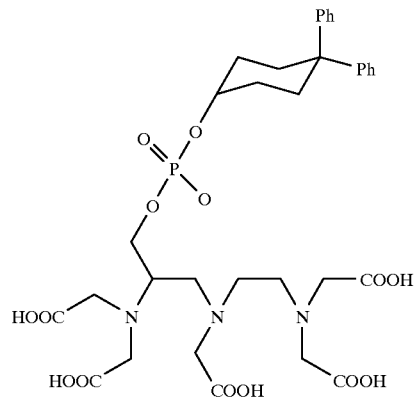

* * * * *